United States Patent [19]

DeVries et al.

[11] Patent Number: 5,082,025
[45] Date of Patent: Jan. 21, 1992

[54] ANTEGRADE-RETROGRADE SWITCH AND OCCLUDER AND SYSTEM FOR USING THE SAME

[75] Inventors: James H. DeVries; Michael R. DeVries, both of Grand Rapids; William E. Sidor, Jr., Rockford; Ronald A. DeVries, Zeeland; Stuart J. Marcadis, Wyoming, all of Mich.

[73] Assignee: DLP, Inc., Grand Rapids, Mich.

[21] Appl. No.: 617,167

[22] Filed: Nov. 23, 1990

[51] Int. Cl.⁵ .................................... F16K 7/02
[52] U.S. Cl. .............................. 137/863; 251/7; 604/248
[58] Field of Search .............. 251/4, 7, 101, 104, 251/297, 288; 137/627.5, 636.1, 863; 604/248, 250

[56] References Cited

U.S. PATENT DOCUMENTS

| | | | |
|---|---|---|---|
| 4,425,116 | 1/1984 | Bilstaad et al. | 251/7 X |
| 4,589,280 | 5/1986 | Carter | 604/248 X |
| 4,616,802 | 10/1986 | Tseng et al. | 251/7 |
| 4,915,132 | 4/1990 | Hodge et al. | 251/297 X |

Primary Examiner—John C. Fox
Attorney, Agent, or Firm—Barnes, Kisselle, Raisch, Choate, Whittemore & Hulbert

[57] ABSTRACT

An apparatus and system for administering cardioplegic solution to a heart during open heart surgery. A source of solution is delivered to a control switch from a single tube source and the tube is divided at a "Y" connector into two tubes, one for antegrade delivery and one for retrograde delivery. The control switch has a prime position with both divided tubes open. Movement from prime position to an operative position is irreversible. In the operative position, there is an "off" position with both tubes closed, an antegrade position with the antegrade tube open and the retrograde tube closed, and a retrograde position with the retrograde tube open and the antegrade tube closed. Movement from one position to the other requires movement through the "off" position so there can be no cross-flow from antegrade to retrograde. Pressure monitoring tubes are incorporated into the switch to be opened and closed with the respective tubes.

20 Claims, 4 Drawing Sheets

ANTEGRADE-RETROGRADE SWITCH AND OCCLUDER AND SYSTEM FOR USING THE SAME

FIELD OF INVENTION

Method and apparatus for controlling cardioplegic solutions to the heart during open-heart surgery.

BACKGROUND AND FEATURES OF THE INVENTION

In open heart surgery, one technique for achieving a motionless heart prior to surgery includes the use of induced hypothermic cardioplegia. This involves the infusion of a cardioplegic solution into the coronary arteries at a low temperature. The chemical composition of the solution varies with different coronary operative teams but one chemical common to all cardioplegic solutions is potassium.

The heart contracts in its normal rhythmic pattern as a result of electrical impulses that are initiated in an area of nerve tissue called the sinoatrial node which is the natural pacemaker for the heart. Potassium in the cardioplegic solution causes an immediate arrest of electrical impulses to the heart. The heart also has a need for oxygen supplied to the heart muscle under normal circumstances The use of a low temperature solution begins to reduce the heart's oxygen consumption rate. The combination of the potassium and the cooling makes it possible for surgeons to perform heart surgery without damage to the heart.

Since it is desirable to arrest heart action for as short a time as possible, the procedures for introduction of the cardioplegic solution must be accomplished as rapidly as possible. The present invention is directed to the control of the supply of the cardioplegic solution to the heart in an efficient manner. The switch may be situated at the cardioplegia source (the heart lung machine or "pump") or at the patient in close proximity to the open chest during the operational procedure. If the device is at the pump, the perfusionist will perform the switching, whereas if it is at the patient, the operating surgeon controls the mechanism. The present disclosure is directed primarily to a unit for use by the operating surgeon. It is generally agreed that myocardial ischemia, that is, withholding the blood from the heart, should be maintained for as brief a period as possible.

The invention involves the use of a supply of cardioplegic fluid which can be applied to the heart at the coronary area in antegrade flow or in the venous area in retrograde flow. With the chest rib cage open, the aorta, which arches over the heart and normally supplies oxygenated blood to the body, is clamped above the heart and an antegrade cannula inserted into the aortic root and sutured. In addition, the coronary sinus is cannulated and a cannula secured for flow into the venous structures of the heart. Thus, there are fluid branches to the aorta and to the venous structures which is the venous side of the heart.

In the extracorporeal system for supplying cardioplegic fluid, a control switch is incorporated at the root of the two fluid branches and, by manually operating the switch, the fluid can be directed to the aorta branch or to the venous side of the heart. The switch has a prime position which allows access to both branches to prime the system. The switch, when moved to an antegrade or retrograde position, operates to close one branch and open the other. The switch is so designed that one branch is closed while the other is open or vice versa. In the switch, pressure monitoring lumens may be incorporated.

The main object then of the control switch is to permit the perfusionist or the surgeon to introduce cardioplegic fluid either to the arterial side of the heart or to the venous side of the heart. In antegrade perfusion if there are occlusions or partial occlusions on the arteries, the cooling may not reach all areas of the heart rapidly. Accordingly, switch to the venous side of the heart (retrograde) furnishes fluid to a large part of the heart and speeds the cardioplegic action. In practice, a portion of the cardioplegia dose can be directed antegrade and the balance of the dose can be directed retrograde.

In addition to the cardioplegic fluid, some heart surgeons utilize ice slush to cool the heart and, in some instances, insulate the far side of the heart from the body.

Additional features and objects of the invention will be apparent in the following description and claims in which details of the invention are set forth, all in connection with the best modes presently contemplated for the practice of the invention.

BRIEF DESCRIPTION OF THE DRAWINGS

DRAWINGS accompany the disclosure and the various views thereof may be briefly described as.

BRIEF DESCRIPTION OF THE INVENTION

The invention is directed to a control switch for administering cardioplegic solution to a heart during open heart surgery. The apparatus is designed to administer the solution in an antegrade phase or a retrograde phase. The switch body has a single supply tube which branches into two lines, antegrade and retrograde. A switch rotor on the body has four positions. One is a prime position wherein both lines are open. This is the shipping position in which neither line is closed and also allows the lines to be open for initial priming with the cardioplegic solution. When the switch rotor is moved 180° out of prime position to an operative position, one of two ramp surfaces, one on either side of the bottom surface of the rotor, moves over a key projection and the high side of the ramps, in the form of a blocking projection, thereafter prevents the rotor from being moved back to the prime position.

With the rotor in the operative position out of prime position, it can have one "off" position when both branches of the branch tubes are closed. It can also have a position away from the "off" position wherein a first branch is open and the second branch closed, or a second position to the other side of the "off" position when the second branch is open and the first branch closed. These positions can be, respectively, for an antegrade flow or a retrograde flow.

Pressure monitoring tubes underlying the branch tubes can be controlled simultaneously by the rotor switch.

DETAILED DESCRIPTION OF THE INVENTION AND THE MANNER AND PROCESS OF USING IT

Figure 1:
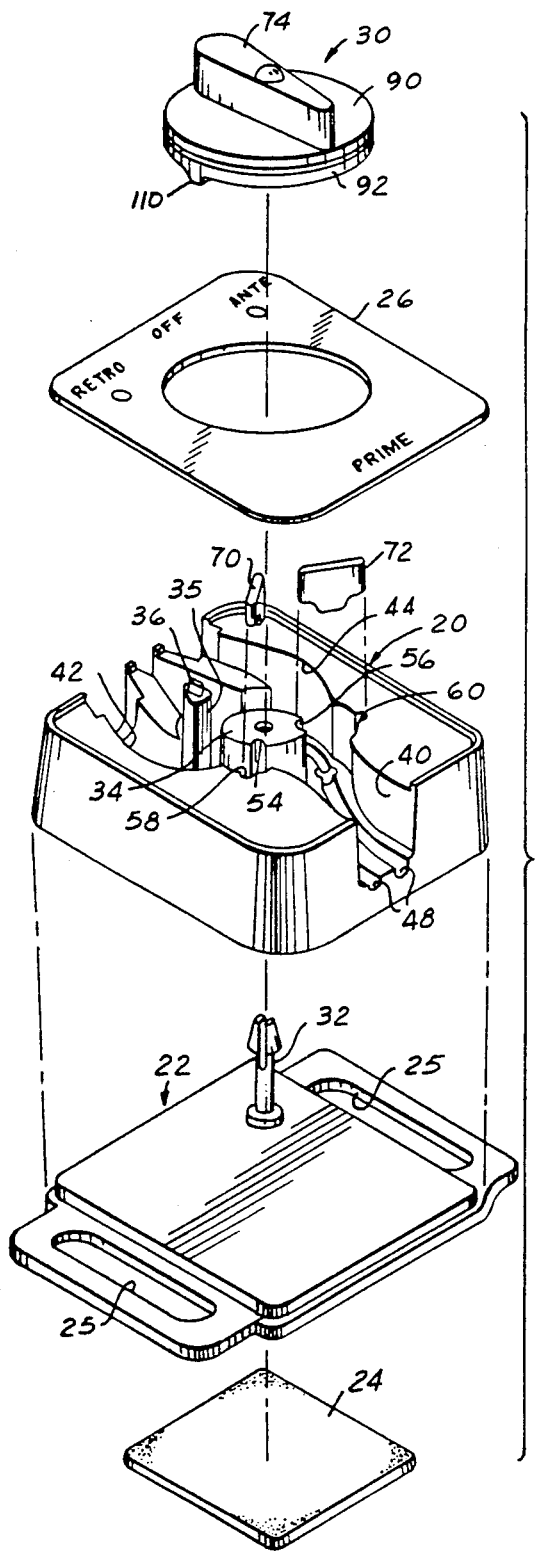
FIG. 1, an exploded view of a control switch showing the various parts in perspective.
Figure 2:
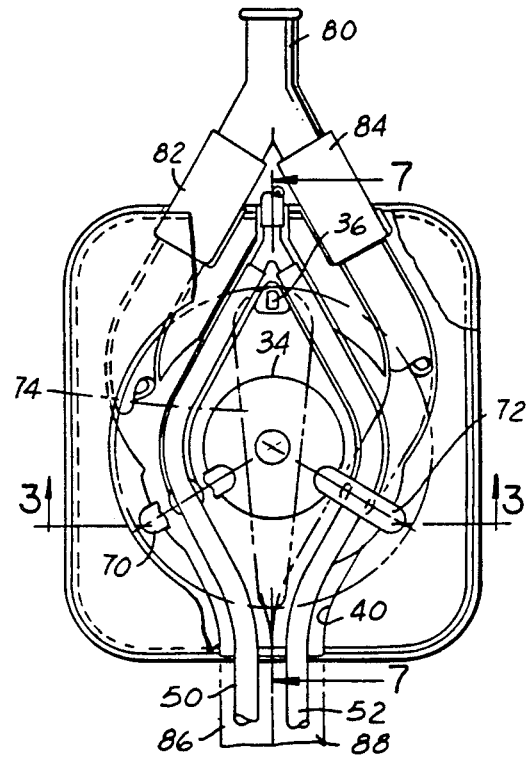
FIG. 2, a plan view of the switchbase and control tubes.
Figure 3:
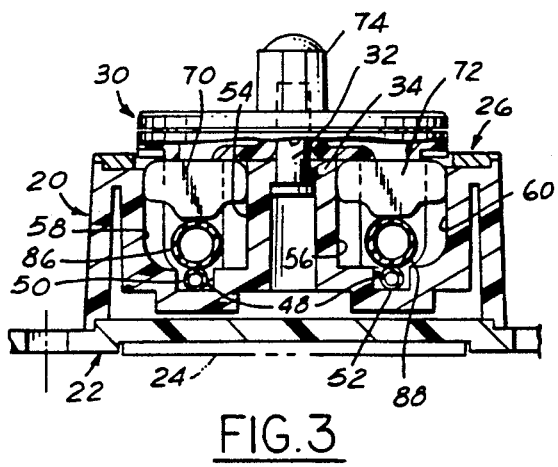
FIG. 3, a full section on line 3—3 of FIG. 2.

With reference to the drawings, in FIGS. 1, 2 and 3 the various parts of the assembly are illustrated. A main body 20 overlies a base plate 22 on the bottom of which is an adhesive pad 24 which allows the switch assembly to be secured to a curtain or fabric area. Side eyelets 25 can be used for placement of clamps. A cover plate 26 will overlie the body 20 and the switch rotor 30 is secured to the body by a split, headed pin 32, the head of which engages a hollow central boss 34 and the split end engages a central recess in the switch rotor 30 to retain the parts in assembly. A central upstanding projection 35 in the body adjacent the boss 34 has a blocking key 36 formed thereon to cooperate with blocking ramps on the bottom of the switch rotor.

The body 20 has a depressed channel 40 diverging into branches 42 and 44 which open on the opposite side of the body. The bottom of the channels 40,42,44 optionally have smaller channels 48 to receive pressure monitoring tubes 50 and 52 seen in FIGS. 2 and 3.

The boss 34 has two circumferentially-spaced, axial grooves 54 and 56 which oppose grooves 58 and 60 in the walls of the diverging channels 42 and 44. These opposed grooves form slide channels for occluders in the form of paddles or detents 70 and 72 (FIG. 2). The switch rotor 30 has a raised diametrical knob 74 which facilitates rotating the rotor 30.

Figure 8:
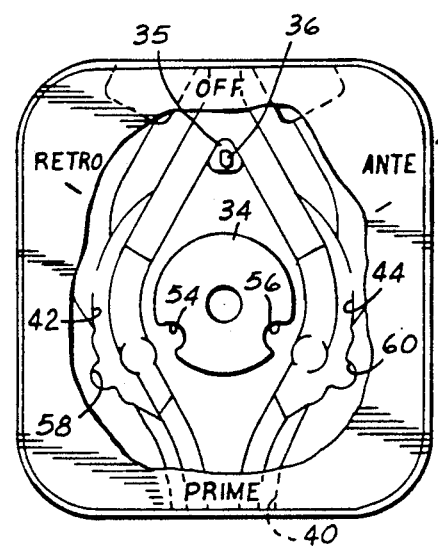
FIG. 8, a top view of the switch body with the cover plate broken away.

FIG. 8 illustrates a plan view of the body 20 with central portions of the top plate 26 cut-away to show the tube passages more clearly. In FIGS. 2 and 3, an inlet source tube 80 for cardioplegic solution divides at a "Y" connection to connectors 82 and 84 leading to flexible tubes 86 and 88 which exit the body at the channel 40. The tubes 86,88 are resilient so that the occluder paddles or detents 70,72 will rise in the respective channels by the resilience of the tubes as will be explained. In the shipping and prime position, the occluder paddles or detents are in the up positions in FIG. 3 so there is no occluding pressure on the tubes in this position.

Figure 5:
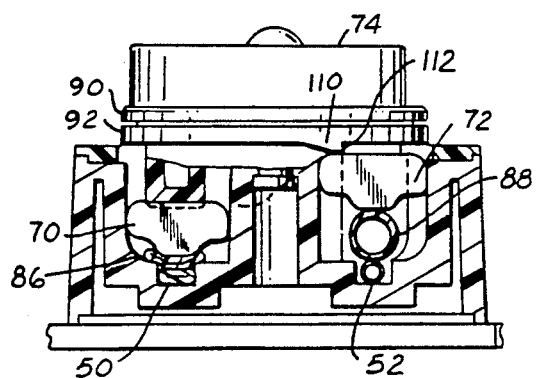
FIG. 5, a view similar to FIG. 3 with one branch of the tube closed and the other open.
Figure 6:
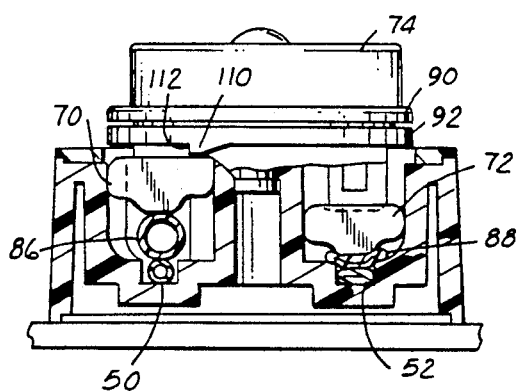
FIG. 6, a view similar to FIG. 3 with an opposite branch closed and the other open.
Figure 7:
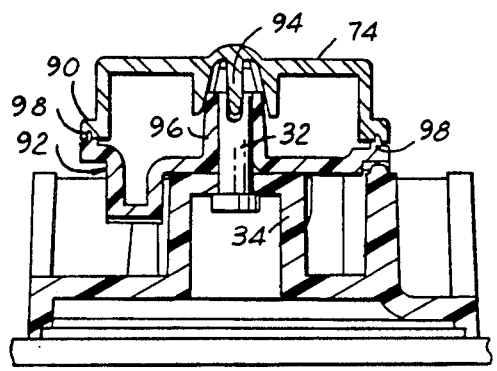
FIG. 7, a section on line 7—7 of FIG. 2 which includes the switch rotor.

The switch rotor 30 is formed of two parts as illustrated in FIGS. 4 to 7. The manual knob 74 is formed on a top plate 90 which is joined to a bottom cam housing 92. The parts are axially secured together by the headed pin 32 which anchors in the boss 34. The pin has a split end (FIG. 1) which in assembly, is cammed outwardly by a depending prong 94 seen in FIG. 7. This urges the prong shoulders outwardly to latch on the rim of the central boss 96 on the lower element 92. As seen in FIG. 7, the rims of the matching parts 90 and 92 are engaged for proper orientation and simultaneous rotation by small projections 98 or are bonded together.

Figure 15:
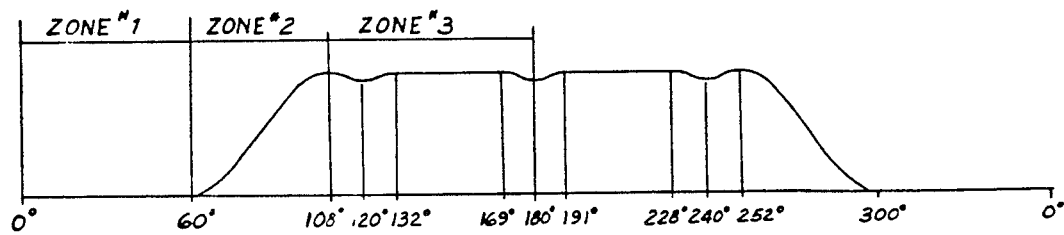
FIG. 15, a development of the contour on the lower side of the switch rotor.

The bottom cam surface of the rotor housing 92 is shaped to control the operative positions of the occluder paddles 70 and 72. This surface is best illustrated in FIGS. 12 to 15. FIG. 15 is a layout development of the surface. A flat section 100 extends about 120° around the cam surface and this surface rises to camming surfaces 102 and 104 between which is a plateau with three detent depressions—A, in the center, and B and C on either side, essentially equally spaced. These detent depressions are shown on the face view of the cam surface in FIG. 14.

Before describing the function of the main operating cam surfaces, a safety configuration should be outlined. Radially outside the main cam surfaces are two spaced short ramps 110. The low end of the surfaces are facing the detent surfaces B and C respectively and the ramps terminate in a blocking surface 112. When the rotor 30 and the knob 74 are in the position called "prime" as illustrated in FIGS. 1, 2 and 3, the occluder paddles 70,72 are in the position shown in FIG. 3 both in the raised position and not pressing on the tubes 86,88. In this position, the flat section 100 of the rotor surface is over the occluder paddles. This is not only the shipping position, which avoids permanent depression of the tubes, but is also a position with both tubes open to permit priming of the system with the cardioplegic solution. Once the priming is accomplished, the rotor is rotated 180°. During this rotation, and regardless of whether it is a clockwise rotation or a counterclockwise rotation, one of the cams 110 will ride over the key projection 36 which will then be located between the locking surfaces 112 of the cams. As a consequence, the rotor cannot be returned to the prime position.

Figure 4:
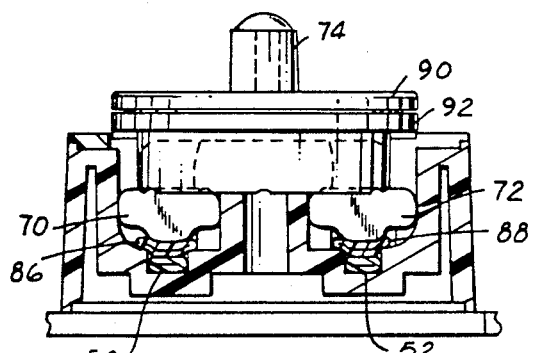
FIG. 4, a view similar to FIG. 3 with both branch tubes closed.
Figure 9:
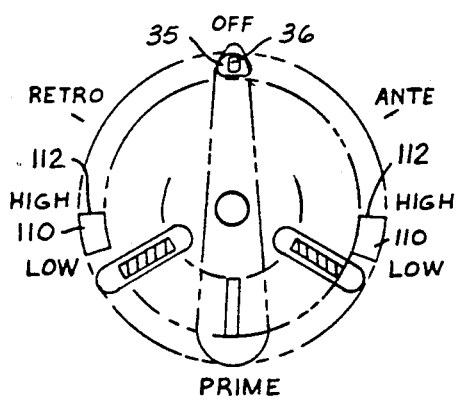
FIG. 9, a diagrammatic view from the top of the switch rotor shown in phantom with detents in section which are engaged in full closed position.

A full 180° rotation of the knob 74, as above described, will place the raised surfaces of the cam (FIG. 15) over the occluder paddles 70,72 as illustrated in FIG. 4. In this position, both tubes are squeezed shut as shown in FIG. 4. The top of the paddles are lodged in the detent depressions B and C respectively. This is shown diagrammatically in FIG. 9.

Figure 10:
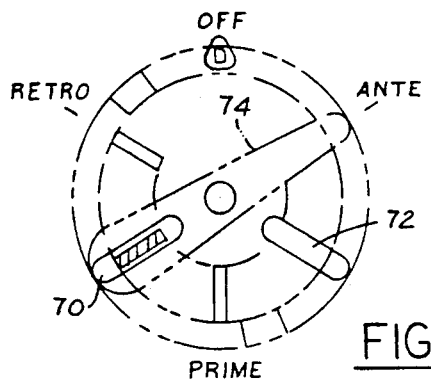
FIG. 10, a view similar to FIG. 9 with a single detent engaged and the passage open in antegrade position.

Now when antegrade flow of the solution is desired, the knob 74 is moved to the right as shown in FIG. 10. In this position, the flat surface 100 overlies the occluders 72 and a cam surface of the rotor moves over the occluder 70 depressing it into the tube 86 and closing off flow from the retrograde tube. The antegrade tube 88 is now open and the retrograde tube 86 is closed as shown in FIG. 5. In this position, the top of the occluder paddle 70 is clicked into the depression A to signal the position and stabilize the rotor.

Figure 11:
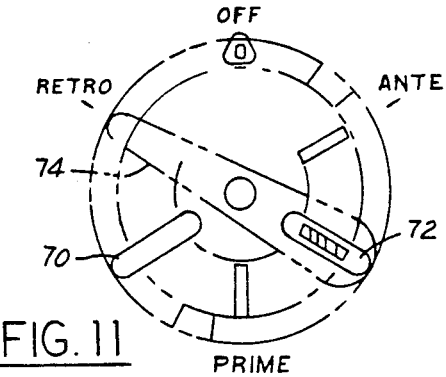
FIG. 11, a view similar to FIG. 9 with a second detent engaged in retrograde position.
Figure 12:
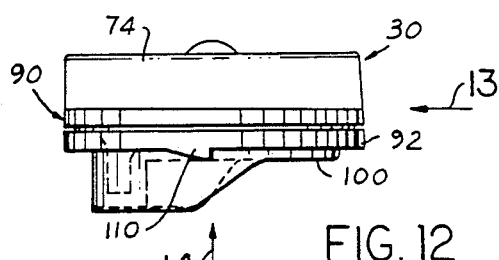
FIG. 12, a side view of the switch rotor.
Figure 13:
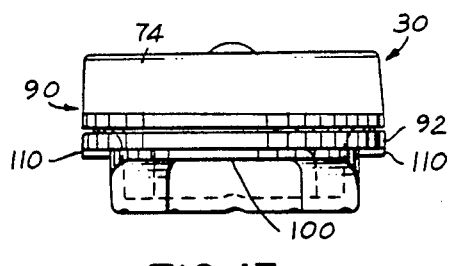
FIG. 13, an end view of the switch rotor on arrow 13 of FIG. 12.
Figure 14:
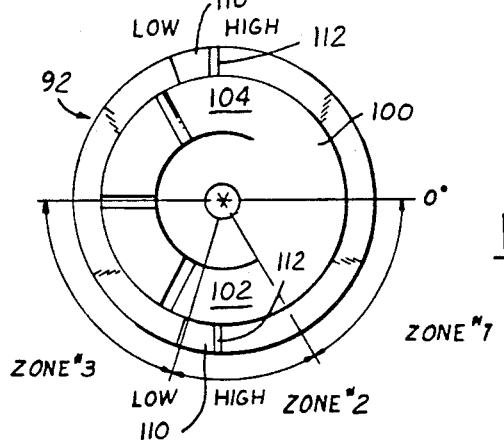
FIG. 14, a bottom view of a switch rotor at arrow 14 of FIG. 12.

When retrograde flow is desired, the knob 74 is rotated counterclockwise to the position shown in FIG. 11. In this rotation the rotor passes the "off" position (FIG. 4) where both tubes are closed and further rotation takes the cam surface to a position where the occluder 70 is under a flat surface 100 of the rotor, and thus tube 86 is in an open position and occluder 72 is depressed to a closed position over tube 88 as shown in FIG. 6. In this position occluder 72 has clicked into the detent depression A.

Thus, once the rotor is moved from the "prime" position with both tubes open, it cannot be moved back due to the blocking surfaces 112 of ramps 110. Also, once out of "prime" position, there can be no cross-flow since in moving from a retrograde to an antegrade position or vice versa, both tubes are momentarily closed, as in FIG. 4, during the motion from one position to the other.

Pressure monitoring is important in both antegrade and retrograde procedures. As shown in FIGS. 3 to 6, pressure monitoring luers are mounted in the smaller grooves underlying the main solution tubes 86,88. These are open and closed by the occluder detents as shown in FIGS. 3 to 6.

Figure 17:
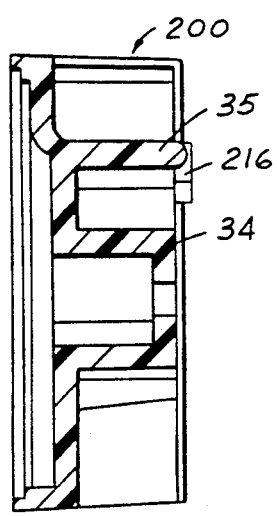
FIG. 17, a sectional view on line 17—17 of FIG. 16.
Figure 16:
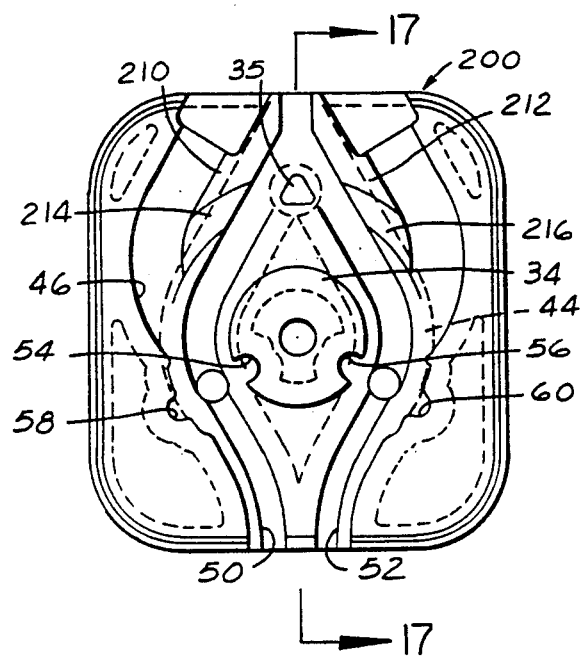
FIG. 16, a view of a modified structure relative to an irreversible block to prime position.

In FIGS. 16 and 17, a modification of the irreversibility feature is illustrated. FIG. 16 is similar to FIG. 8 as to the main body 200 with the exception that the blocking key 36 on projection 35 is removed. The base 200 has delta shaped key projections 210 and 212 on either side of projection 35 and, on the upper surface of these delta projections 210,212, are raised islands 214 and 216. Ramps 110 illustrated in FIG. 9 on the outer flange of the top rotor part 90 cooperate with these islands. When rotor 90 is in the prime position, the ramps 110 are both below the islands 214,216. When the rotor is rotated 180° to the "OFF" position, and depending on the direction of rotation, one of the ramps 110 will lift and ride over an island. Once this happens, the rotor cannot be reversed back to the prime position because of the interference of the high side of the ramp with the lower end of an island.

Thus, with this embodiment, as in the previous modification, once the rotor is moved out of "prime" position to an "off" position, it cannot be turned to "prime" again. Also, the movement from "off" position to antegrade or movement from antegrade to retrograde always involves going through the "off" position so there can be no cross-flow.

Figure 18:
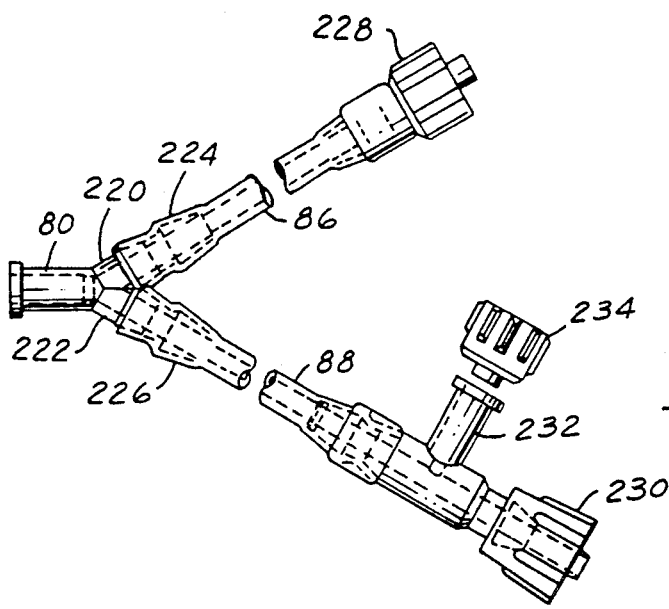
FIG. 18, a view of a "Y" tube connection for a cardioplegic switch.

In FIG. 18, a "Y" connection has a root connector 80 with branches 220 and 222 which mount in the body of switch 20 or 200. Connectors 224 and 226 slip on to branches 220 and 222 and hold luers 86 and 88 as viewed in FIG. 2. A retrograde connector 228 at the end of luer 86 will connect to a heart stylet at the aorta of the heart. At the end of the luer 88 is a connector 230 for antegrade catheter leading to the venous structures of the heart. A branch connection 232 has a ribbed male luer cap 234 to close off the branch 232. If desired, this cap can be removed and the branch connected to a line pressure monitor distal to the cannula. This connector may also be used to distend saphenous veins prior to insertion to check for leakage.

Figure 19:
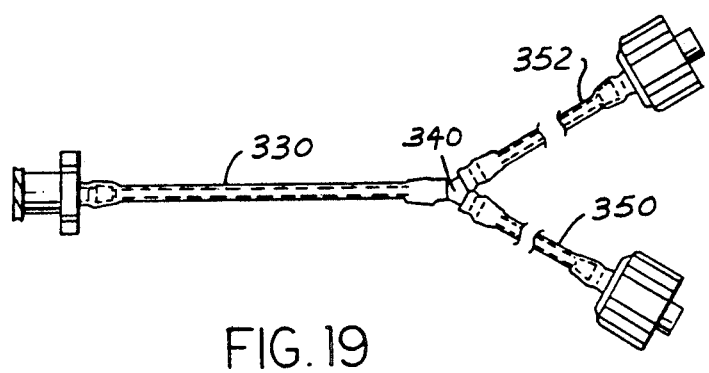
FIG. 19, a view of a "Y" tube connection for a pressure monitoring circuit.

In FIG. 19, the pressure monitor "Y" is illustrated with a stem 330 divided at 340 into passages 350 and 352 (50 and 52 in FIG. 2) which lie within the switch body 20 and 200 below the main retrograde and antegrade tubes.

What is claimed is:

1. A method for administering antegrade-retrograde cardioplegic solution to a heart during open heart surgery which comprises the steps of:
   (a) providing a source of cardioplegic solution,
   (b) dividing the source into an antegrade supply and a retrograde supply,
   (c) opening both supplies to a prime position for priming,
   (d) providing a switch control for opening one while closing the other of said antegrade supply and said retrograde supply,
   (e) providing an position on said switch control to close both supplies, and
   (f) moving the switch control through the off position in each move from antegrade to retrograde and vice-versa to insure no cross-flow between the antegrade supply and the retrograde supply.

2. A method as in claim 1 comprising the additional steps of providing pressure monitoring luers associated with each of said supplies, and moving the switch control to close associated luers when closing said respective supplies.

3. The method set forth in claim 1 comprising the additional step of blocking return to said prime position in said step (c) following movement of said switch control to any position as set forth in said step (f).

4. A control for administering antegrade and retrograde cardioplegic solution to a heart during open heart surgery which comprises:
   (a) a control switch body having divided first and second passages for parallel antegrade and retrograde flow.
   (b) means in said body movable from a position to open said passages and to a position to close said passages,
   (c) a switch rotor having cam surfaces to actuate said means in various rotated positions of said rotor, sequentially to open both passages in a prime position, close both said passages in an off position, open a first passage and close a second passage in an antegrade position, and open a second passage and close a first passage in a retrograde position, and
   (d) blocking means on said body for blocking said rotor from movement to said prime position in which both said passages are open after movement from said prime position to an off position or to an antegrade or retrograde position.

5. A control for administering antegrade and retrograde cardioplegic solution to a heart during open heart surgery as defined in claim 4 in which said blocking means comprises engageable first means on said body and second means on said switch rotor, one of said first and second engageable means having a ramp surface to ride over the other of said first and second engageable means in one direction of rotation of said rotor and to be blocked against reverse rotation of said rotor in an opposite direction of rotation.

6. A control for administering antegrade and retrograde cardioplegic solution to a hear during open heart surgery as defined in claim 5 in which said first means on said body comprises a stationary central upstanding projection in said body having a key projection to be contacted by a ramp surface on a second means which ridges over said key projection in one direction of rotation of said rotor and being blocked against reversal movement in the other direction by a high end of a ramp surface.

7. A control for administering antegrade and retrograde cardioplegic solution to a hear during open heart surgery as defined in claim 5 in which said first means on said body comprises circumferentially spaced islands upstanding in said body to be contacted by one of circumferentially spaced ramp surfaces on said rotor, said ramp surfaces riding up and over one of said islands in a direction of rotation and being blocked against reversal movement by a high end of said ramp surface and an island.

8. A control for administering antegrade and retrograde cardioplegic solution to a heart during open heart surgery as defined in claim 4 in which resilient, flexible tubes are disposed in said first and second passages, and said means in said body movable from a position to open and close said passages comprise occluders respectively mounted transversely of said passages, and positioned to be moved against said tubes to compress the tubes to a closed position when contacted by a cam surface of said switch rotor.

9. A control for administering antegrade and retrograde cardioplegic solution to a heart during open heart surgery as defined in claim 8 in which said occluders comprise paddles each mounted in opposed grooves in said switch body overlying one of said passages in said switch body and confined by and underlying said cam surfaces of said switch rotor.

10. A control for administering antegrade and retrograde cardioplegic solution to a heart during open heart surgery as defined in claim 8 in which said cam surfaces include a relatively flat surface which is located over said occluders in the prime position of said rotor leaving said tubes pen, and rising cam surfaces on each side of a main raised cam surface to cam said occluders into closed positions, respectively to an off position midway of said raised surfaces with both tubes closed, an antegrade position in which a first of said occluders is depressed by a cam surface and the second is under a flat surface to open a first tube, and a retrograde position in which said first of said occluders is under a flat surface to open a tube and said second of said occluders is depressed by a cam surface to close the second tube.

11. A control for administering antegrade and retrograde cardioplegic solution to a heart during open heart surgery as defined in claim 4 in which said control switch body has a central upstanding boss between said first and second passages, said switch rotor having a central aperture to overlie said boss, and a retainer pin protruding upwardly from said boss, the end of which is anchored in said rotor to retain the body and the rotor in operative relation.

12. A control for administering antegrade and retrograde cardioplegic solution to a heart during open heart surgery as defined in claim 11 in which said retainer pin is split axially, and in which a depending projection in said rotor enters said pin and spreads it radially during assembly to lock the pin in the rotor.

13. A system for administering antegrade-retrograde cardioplegic solution to a heart during open heart surgery that comprises:
   means for connection to a source of cardioplegic solution,
   means for dividing flow of fluid from said source into an antegrade supply and a retrograde supply,
   means for opening both said supplies to a prime position for priming the system, and
   a switch control for opening one while closing the other of said antegrade supply and said retrograde supply.
   said switch control having an off position in which both of said supplies are closed,
   said switch control being movable through the off position in each move from antegrade to retrograde and vice-versa to insure no cross-flow between the antegrade supply and the retrograde supply, and
   means blocking return to said prime position following movement of said switch control to any of said off, antegrade supply and retrograde supply positions.

14. A system as in claim 13 in which pressure monitoring luers are associated with each of said supplies, and in which said switch control is movable to close associated luers when closing said respective supplies.

15. A control for administering antegrade and retrograde cardioplegic solution to a heart during open heart surgery which comprises:
   (a) a control switch body having divided first and second passages for parallel antegrade and retrograde flow,
   (b) means in said body movable from a position to open said passages and to a position to close said passages,
   (c) a switch rotor having cam surfaces to actuate said means in various rotated positions of said rotor, to open both passages in a prime position, close both said passages in an off position, open a first passage and close a second passage in an antegrade position, and open a second passage and close a first passage in a retrograde position, and
   resilient flexible tubes disposed in said first and second passages, said means in said body movable from a position to open and close said passages comprising occluders respectively mounted transversely of said passages and positioned to be moved against said tubes to compress the tubes to a closed position when contacted by a cam surface of said switch rotor,
   said cam surfaces including a relatively flat surface that is located over said occluders in the prime position of said rotor leaving said tubes open, and rising cam surfaces on each side of a main raised cam surface to cam said occluders into closed positions, respectively to an off position midway of said raised surfaces with both tubes closed, an antegrade position in which a first of said occluders is depressed by a cam surface and the second is under a flat surface to open a first tube, and a retrograde position in which said first of said occluders is under a flat surface to open a tube and said second of said occluders is depressed by a cam surface to close the second tube.

16. A control for administering antegrade and retrograde cardioplegic solution to a heart during open heart surgery as defined in claim 15 which includes blocking means on said body for blocking said rotor from movement to said prime position in which both said passages are open after movement from said prime position to an off position or to an antegrade or retrograde position.

17. A control for administering antegrade and retrograde cardioplegic solution to a heart during open heart surgery as defined in claim 15 in which said main raised surface has three detent notches to receive, respectively, an edge of an occluder to define respective positions of flow an antegrade, off, and retrograde, said off position lying between said antegrade and retrograde positions wherein movement between antegrade and retrograde positions always requires movement through said off position.

18. A control for administering antegrade and retrograde cardioplegic solution to a heart during open heart surgery which comprises:
   (a) a control switch body having divided first and second passages for parallel antegrade and retrograde flow,
   (b) means in said body movable from a position to open said passages and to a position to close said passages, and
   (c) a switch rotor having cam surfaces to actuate said means in various rotated positions of said rotor, to sequentially open both passages in a prime position, close both said passages in an off position, open a first passage and close a second passage in an antegrade position, and open a second passage and close a first passage in a retrograde position,
   said control switch body having a central upstanding boss between said first and second passages, said switch rotor having a central aperture to overlie said boss and a retainer pin protruding upwardly from said boss, the end of which is anchored in said rotor to retain the body and the rotor in operative relation, said retainer pin being split axially, a depending projection in said rotor entering said pin and spreading it radially during assembly to lock the pin in the rotor.

19. A control for administering antegrade and retrograde cardioplegic solution to a heart during open heart surgery that comprises:
   a control switch body having divided first and second passages for antegrade and retrograde flow respectively,
   means on said body movable from positions to open said passages to positions to close said passages,
   a switch rotor having cam surfaces to actuate said means in various rotative positions of said rotor to open one of said passages and close the other in a first position of said rotor, to close said one passage and open said other passage in a second position of each rotor, and to close both of said passages in a third position of said rotor, and
   means on said body blocking rotation of said rotor from said first position to said second position except through said third position to prevent cross flow between said passages.

20. The control set forth in claim 19 wherein said switch rotor is positionable on said body at a fourth position in which both of said passages are open, and in which said means on said body blocks movement of said rotor to said fourth position from any one of said first, second and third positions.

* * * * *

UNITED STATES PATENT AND TRADEMARK OFFICE
CERTIFICATE OF CORRECTION

PATENT NO. : 5,082,025
DATED : January 21, 1992
INVENTOR(S) : James H. DeVries et al It is certified that error appears in the above—identified patent and that said Letters Patent is hereby corrected as shown below:

Col. 6, Line 8, after "an" insert — off —.

Col. 6, Line 56, change "hear" to — heart —.

Col. 6, Line 61, change "ridges" to — rides —.

Col. 6, Line 66, change "hear" to — heart —.

Col. 8, Line 66, change "an" to — as —.

Signed and Sealed this

First Day of June, 1993

Attest:

MICHAEL K. KIRK

Attesting Officer   Acting Commissioner of Patents and Trademarks